United States Patent
Rao et al.

(10) Patent No.: US 7,351,840 B2
(45) Date of Patent: Apr. 1, 2008

(54) PERINDOPRIL

(75) Inventors: Dharmaraj Ramachandra Rao, Maharashtra (IN); Rajendra Narayanrao Kankan, Maharashtra (IN)

(73) Assignee: Cipla Limited, Mumbai, Mumbai Central (IN)

( * ) Notice: Subject to any disclaimer, the term of this patent is extended or adjusted under 35 U.S.C. 154(b) by 0 days.

(21) Appl. No.: 10/535,187

(22) PCT Filed: Nov. 18, 2003

(86) PCT No.: PCT/GB03/04981

§ 371 (c)(1),
(2), (4) Date: Oct. 31, 2005

(87) PCT Pub. No.: WO2004/046172

PCT Pub. Date: Jun. 3, 2004

(65) Prior Publication Data

US 2006/0063941 A1    Mar. 23, 2006

(30) Foreign Application Priority Data

Nov. 18, 2002  (GB) ................................. 0226885.2

(51) Int. Cl.
*C07D 209/12* (2006.01)
*A61K 31/405* (2006.01)
(52) U.S. Cl. ...................... 548/515; 514/186
(58) Field of Classification Search ................. 548/514
See application file for complete search history.

(56) References Cited

U.S. PATENT DOCUMENTS 4,508,729 A * 4/1985 Vincent et al. ............. 514/419
4,914,214 A    4/1990 Vincent et al.
6,932,983 B1 * 8/2005 Straub et al. ............... 424/489

FOREIGN PATENT DOCUMENTS

EP    1647547    4/2006
JP    2001122780    5/2001

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the internet, URL; http://www.cnn.com/2003/HEALH/conditions/09/24/alzheimers.drug.ap/index.html>.*
Cognitive disorder [online], [retrieved on Sep. 1, 2006]. Retrieved from the Internet, URL; http://en.wikipedia.org/wiki/Category:Cognitive_disorders>.*
Das, U. Is angiotensin II an endogenous pro-inflammatory molecule? Med Sci Monit, 2005, vol. 11, p. RA155-162.*

Vincent M et al: "Stereoselective Synthesis of a New Perhydroindole Derivative of Chiral Iminodiacid, a Potent Inhibitor of Agiotensin Converting Enzyme"; Tetrahedron, Elsevier Science Publishers, Amsterdam, NL, vol. 23, No. 16, 1982, pp. 1677-1680.
Vincent M et al: "Synthesis and Ace Inhibitory Activity of the Stereoisomers of Perindopril (S 9490) and Perindoprilate (S 9780)"; Drug Design and Discovery, Harwood Academic Publishers GMBH, XX, vol. 9, No. 1, 1992, pp. 11-28.
Search Report dated Feb. 17, 2004.
Partial European Search Report dated Jul. 5, 2006 from corresponding European Patent Application No. 06 07 6083.2.
Vincent M et al., "Stereoselective Synthesis of a New Perhydroindole Derivative of Chiral Iminodiacid, a Potent Inhibitor of Agiotensin Converting Enzyme", TETRAHEDRON, Elsevier Science Publishers, Amsterdam, NL, vol. 23, No. 16, 1982, pp. 1677-1680, XP002155080, ISSN: 0040-4020, the whole document.
Vincent M et al., "Synthesis and Ace Inhibitory Activity of the Stereoisomers of Perindopril (S 9490) and Perindoprilate (S 9780)", Drug Design and Discovery, Harwood Academic Publishers GMBH, XX, vol. 9, No. 1, 1992, pp. 11-28, XP000885876, ISSN: 1055-9612, p. 18.

(Continued)

*Primary Examiner*—Rebecca Anderson
*Assistant Examiner*—Shawquia Young
(74) *Attorney, Agent, or Firm*—Stevens, Davis, Miller & Mosher LLP

(57) ABSTRACT

A pharmaceutically acceptable salt of perindopril of formula (I) is made from a protected precursor compound of formula (II) wherein R represents a carboxyl protecting group, which process comprises subjecting a compound of formula (II) to deprotection of the carboxylic group COOR attached to the heterocyclic ring so as to yield the corresponding free acid, which deprotection is carried out in the presence of a base which forms a pharmaceutically acceptable salt with the free acid formed by the deprotection

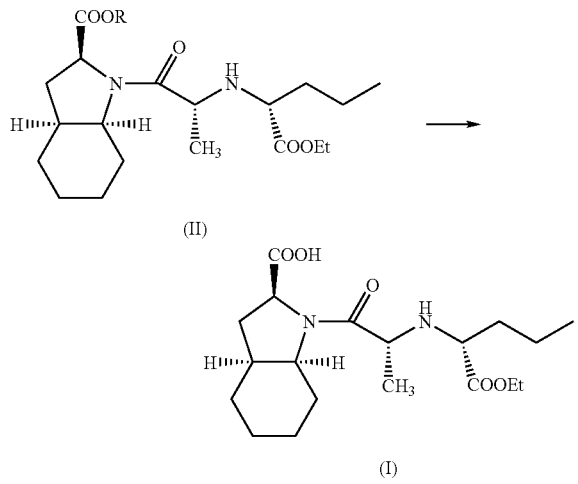

15 Claims, 1 Drawing Sheet

OTHER PUBLICATIONS

Hillaert S et al., "Optimization of capillary electrophoretic separation of several inhibitors of the angiotensin-converting enzyme", Journal of Chromatography, Elsevier Science Publishers B.V. Amsterdam, NL, vol. 895, No. 1-2, Oct. 20, 2000, pp. 33-42, XP004217478, ISSN: 0021-9673 p. 35.

* cited by examiner

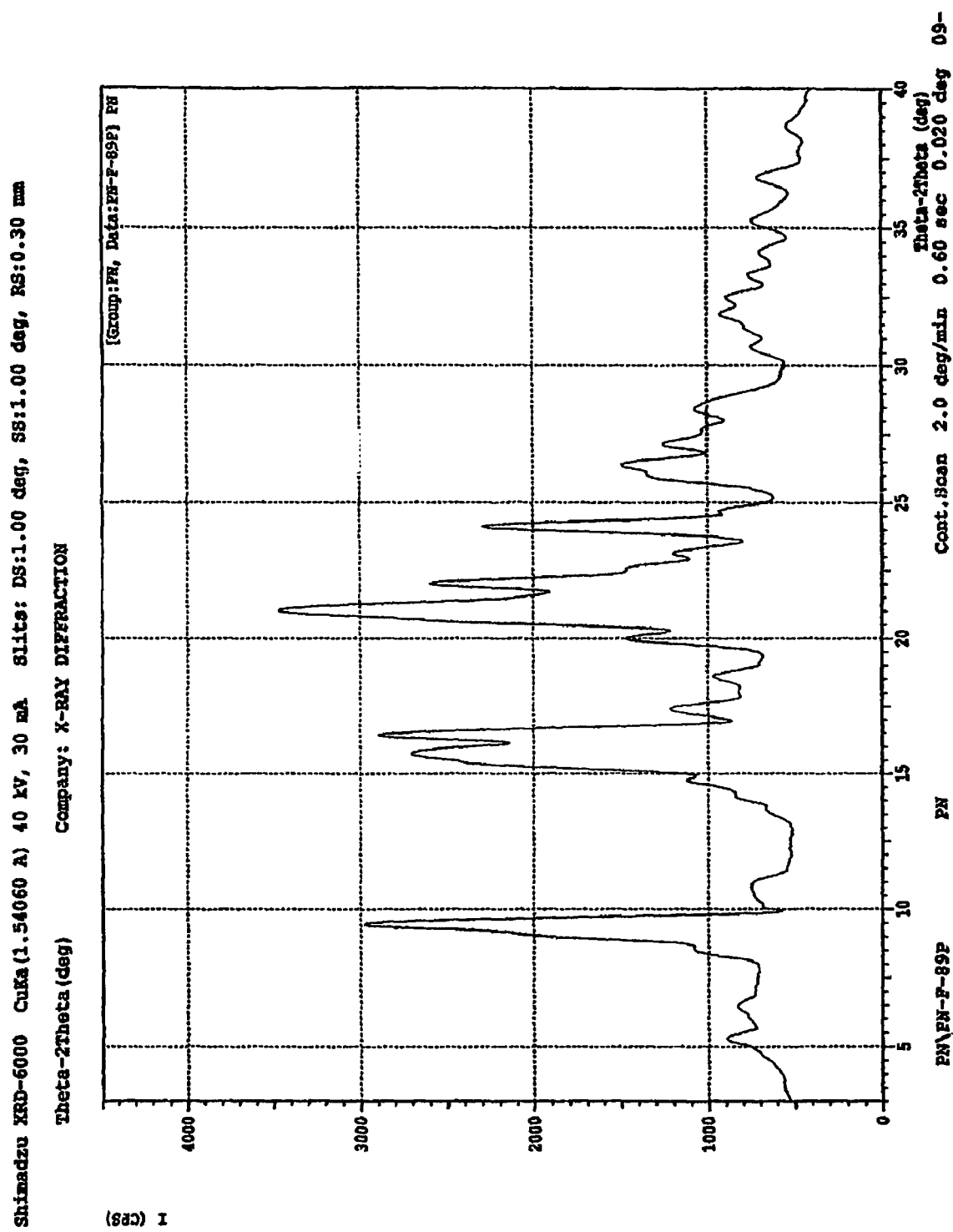

PERINDOPRIL

This application is a 35 U.S.C. §371 U.S. National Stage Application of International Application No. PCT/GB2003/004981, filed on Nov. 18, 2003, claiming the priority of Great Britain Application No. 0226885.2, filed Nov. 18, 2002, the entire disclosures of which are incorporated herein by reference in their entireties.

This invention relates to a process for preparing a pharmaceutically acceptable salt of perindopril, and a novel polymorphic form thereof.

Perindopril is the international non-proprietary name of (2S,3aS,7aS)-1-{2-[1-(ethoxycarbonyl)-(S)-butylamino]-(S)-propionyl}-octahydroindole-2-carboxylic acid. Perindopril is known to have therapeutic application as an angiotensin—converting enzyme (ACE) inhibitor. ACE is a peptidyl dipeptidase which catalyzes the conversion of angiotensin I to angiotensin II, as well as causing the degradation of bradykinin. Angiotensin II is a vasoconstrictor which also stimulates aldosterone secretion by the adrenal cortex. Inhibition of ACE has, therefore, been shown to have therapeutic utility in patients suffering from disease states such as hypertension and congestive heart failure. In addition, it has been discovered that ACE inhibitors are useful in treating cognitive disorders.

Perindopril has the following structural formula (I)

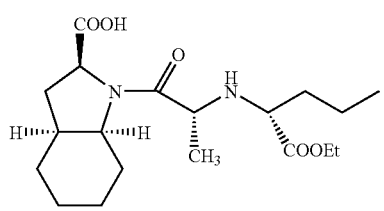

(I)

Perindopril is described in U.S. Pat. No. 4,508,729. Preparative processes described in this U.S. patent are carried out in an alcoholic medium, and in the presence of a neutral dehydrating agent and an organic or inorganic cyanoborohydride. Deprotection processes can be carried out where necessary, for example with reference to hydrolysis and/or hydrogenolysis.

U.S. Pat. No. 4,914,214 describes a process for the preparation of perindopril and its t-butylamine salt. The process comprises condensation of a protected ester of (2S,3aS,7aS)-2-carboxyperhydroindole with the (S,S) diastereoisomer of N-[(S)-1-carbethoxybutyl]-(S)-alanine, followed by deprotection employing charcoal containing 5% palladium and water. Tertiary-butylamine is then added to yield the t-butylamine salt of perindopril.

PCT patent application WO 01/87835 describes a novel crystalline form, namely α crystalline form, of the t-butylamine salt of perindopril, processes of preparing the same and pharmaceutical formulations containing the same.

PCT patent application WO 01/87836 describes a novel crystalline form, namely ∃ crystalline form, of the t-butylamine salt of perindopril, processes of preparing the same and pharmaceutical formulations containing the same.

PCT patent application WO 01/87835 describes a novel crystalline form, namely γ crystalline form, of the t-butylamine salt of perindopril, processes of preparing the same and pharmaceutical formulations containing the same.

PCT patent application WO 01/58868 describes a process of preparing perindopril or pharmaceutically acceptable salts thereof, which process provides perindopril, or a salt thereof, with improved purity. More particularly, the level of known impurities associated with perindopril or a salt thereof, prepared according to PCT patent application WO 01/58868, is described as being less than 0.2 or 0.1% by weight. Intermediate process steps are carried out in the presence of 1-hydroxybenzotriazole, dicyclohexylcarbodiimide and optionally triethylamine, and at a temperature in the range of 20 to 77 EC, followed by deprotection and where required salt conversion.

Prior art processes for the preparation of perindopril, or pharmaceutically acceptable salts thereof, have generally tended to be time-consuming and have often resulted in undesirable associated impurities, such as diketopiperazine analogues. There is, therefore, a need for an improved process for preparing perindopril, or pharmaceutically acceptable salts thereof, which alleviates the above mentioned problems.

We have now developed a process for preparing a pharmaceutically acceptable salt of perindopril, which is advantageous in terms of a faster reaction time compared to known processes for the preparation of a pharmaceutically acceptable salt of perindopril, and also in obviating the production of undesirable impurities so as to achieve a highly pure product.

In accordance with one aspect of the present invention, there is provided a process for preparing a pharmaceutically acceptable salt of perindopril of formula (I) from a protected precursor compound of formula (II)

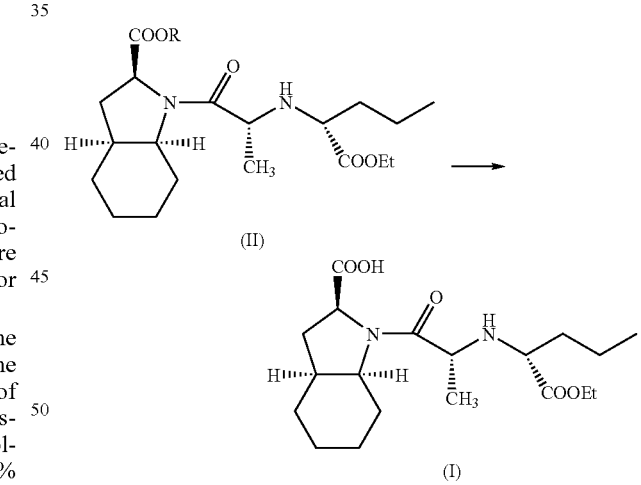

wherein R represents a carboxyl protecting group, which process comprises subjecting a compound of formula (II) to deprotection of the carboxylic group COOR attached to the heterocyclic ring so as to yield the corresponding free acid, which deprotection is carried out in the presence of a base which forms a pharmaceutically acceptable salt with said free acid formed by said deprotection.

Typically, R can represent any suitable carboxyl protecting group that can be selectively removed by a process according to the present invention. Preferably, R can represent optionally substituted aralkyl, especially optionally substituted benzyl. R can, therefore, typically represent unsubstituted benzyl; alternatively substituted benzyl can be employed, such as 4-halo substituted, or 4-C$_{1-4}$alkoxy substituted benzyl, especially 4-Clbenzyl, or 4-methoxy benzyl.

Suitably, deprotection as employed in a process according to the present invention can comprise hydrogenolysis in the presence of a noble metal catalyst, preferably palladium-on-chacoal.

The process of the present invention is advantageous in achieving a highly pure product. A pharmaceutically acceptable salt of perindopril prepared by a process according to the present invention is preferably more than about 99% w/w pure, and more preferably more than about 99.5% w/w pure. The purity of a pharmaceutically acceptable salt of perindopril prepared by a process according to the present invention can be further enhanced by an optional crystallisation step in a suitable solvent, such as ethyl acetate, isopropanol or the like, so as to obtain a pharmaceutically acceptable salt of perindopril which is preferably about 99.8% w/w pure.

Preferably, the base employed in the process of the present invention is selected so as to form a pharmaceutically acceptable salt with the free acid formed by the deprotection as indicated above, whereby it is possible to obtain a pharmaceutically acceptable salt of perindopril directly from such a reaction work-up. In a particularly preferred embodiment according to the present invention the base comprises t-butylamine and as such a preferred process according to the present invention can provide a highly pure t-butylamine salt of perindopril directly from the reaction process.

According to the above preferred embodiment of the present invention, there is provided a process for preparing perindopril t-butylamine (which is well known to those of skill in the art as being perindopril erbumine) from a protected precursor compound of formula (II) substantially as hereinbefore described (preferably a benzyl protected precursor compound of formula (II) where R represents benzyl), which process comprises subjecting a compound of formula (II) to deprotection (preferably hydrogenolysis in the presence of a noble metal catalyst such as palladium-on-chacoal) of the carboxylic group COOR attached to the heterocyclic ring so as to yield the corresponding free acid, which deprotection is carried out in the presence of t-butylamine so as to form the t-butylamine salt of perindopril.

Suitably a precursor compound of formula (II) is initially dissolved in an alkanol solvent, such as isopropanol or the like, followed by addition of the base thereto. This is further followed by the deprotection of the carboxylic group COOR, suitably by the addition of palladium-on-charcoal and hydrogenation for several hours. The alkanol solvent is suitably concentrated under vacuum and replaced by a water immiscible solvent, such as ethyl acetate or the like. The resulting solids can then be cooled and filtered to yield a pharmaceutically acceptable salt of perindopril.

The process according to the present invention substantially as hereinbefore described may further comprises hydrating a pharmaceutically acceptable salt of perindopril obtained by the process so as to yield a pharmaceutically acceptable salt of hydrated perindopril of formula (Ia)

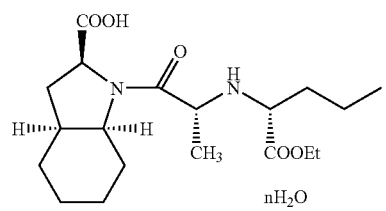

(Ia)

wherein n is an integer of 1 to 5, or a reciprocal of integers 2 to 5. Hydration can be by way of the addition of water or by drying in air.

Preferably n is 1, whereby a pharmaceutically acceptable salt of perindopril monohydrate is formed by a process according to the present invention.

The present invention also provides a process for preparing a monohydrate of a pharmaceutically acceptable salt of perindopril, which process comprises hydrating a pharmaceutically acceptable salt of perindopril so as to yield said monohydrate. Hydration can be by way of the addition of water or by drying in air, and preferably perindopril t-butylamine is hydrated to yield perindopril t-butylamine monohydrate.

The present invention further provides a pharmaceutically acceptable salt of perindopril optionally in hydrated form, prepared by a process substantially as hereinbefore described. In particular, a pharmaceutically acceptable salt of hydrated perindopril of formula (Ia) is provided

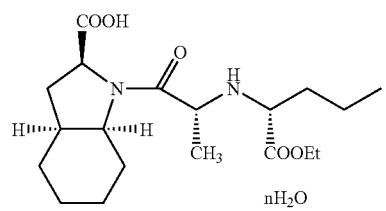

(Ia)

wherein n is an integer of 1 to 5, or a reciprocal of integers 2 to 5. Preferably, n is 1. A preferred pharmaceutically acceptable salt of hydrated perindopril of formula (Ia) is the t-butylamine salt. In a particularly preferred embodiment, the present invention provides perindopril t-butylamine (or erbumine) monohydrate.

The present invention also provides perindopril t-butylamine monohydrate having an X-ray diffractogram, or substantially the same X-ray diffractogram, as set out in FIG. 1. More particularly, perindopril t-butylamine monohydrate according to the present invention can be characterised as having an X-ray powder diffraction pattern with characteristic peaks (2θ): 9.5504, 14.8600, 15.7486, 16.5400, 20.0400, 21.0499, 22.0600, 24.1744, 26.3300 and 27.1600.

Further characterising data for perindopril t-butylamine monohydrate according to the present invention as obtained by X-ray diffraction is shown in following Table 1.

TABLE 1

| Peak No. | 2θ (deg) | d (A) | I/Il | FWHM (deg) | Intensity (Counts) | Integrated I (Counts) |
|---|---|---|---|---|---|---|
| 1 | 8.6400 | 10.22611 | 10 | 0.57600 | 151 | 6899 |
| 2 | 9.5504 | 9.25324 | 73 | 0.50470 | 1090 | 28204 |
| 3 | 10.5940 | 8.34394 | 5 | 0.97200 | 79 | 4071 |
| 4 | 13.6000 | 6.50569 | 6 | 0.42860 | 91 | 2112 |
| 5 | 14.1400 | 6.25844 | 14 | 0.47120 | 215 | 5210 |
| 6 | 14.8600 | 5.95678 | 22 | 0.59000 | 332 | 10293 |
| 7 | 15.7486 | 5.62262 | 75 | 0.14270 | 1111 | 49244 |
| 8 | 16.5400 | 5.35533 | 30 | 0.72500 | 450 | 15749 |
| 9 | 17.5400 | 5.05220 | 16 | 0.67120 | 231 | 9128 |
| 10 | 18.6100 | 4.76406 | 17 | 0.56000 | 249 | 7981 |
| 11 | 20.0400 | 4.42722 | 31 | 0.51660 | 458 | 13471 |
| 12 | 21.0499 | 4.21704 | 100 | 0.90700 | 1488 | 63860 |
| 13 | 22.0600 | 4.02618 | 50 | 0.59480 | 747 | 23998 |
| 14 | 23.1600 | 3.83738 | 17 | 0.71720 | 253 | 12014 |
| 15 | 24.1744 | 3.67860 | 47 | 0.50030 | 705 | 17912 |
| 16 | 24.8000 | 3.58721 | 5 | 0.26000 | 73 | 1463 |
| 17 | 26.3300 | 3.38213 | 31 | 0.94000 | 468 | 19402 |
| 18 | 27.1600 | 3.28062 | 20 | 0.68500 | 292 | 9230 |
| 19 | 28.4444 | 3.13534 | 15 | 0.96890 | 223 | 11023 |
| 20 | 30.8000 | 2.90071 | 7 | 0.59340 | 99 | 3196 |
| 21 | 31.8000 | 2.81173 | 9 | 0.65600 | 130 | 4356 |
| 22 | 32.5600 | 2.74782 | 11 | 0.61340 | 163 | 4411 |
| 23 | 33.2400 | 2.69314 | 6 | 0.75000 | 95 | 3116 |
| 24 | 34.1800 | 2.62120 | 4 | 0.64000 | 61 | 2155 |
| 25 | 35.4728 | 2.52857 | 7 | 0.85430 | 104 | 4353 |
| 26 | 36.8838 | 2.43502 | 6 | 0.61900 | 93 | 2985 |
| 27 | 38.7340 | 2.32285 | 4 | 0.50800 | 55 | 1432 |

Perindopril as provided by the present invention has therapeutic utility as an ACE inhibitor.

In addition, the present invention further provides a method of inhibiting ACE in a patient in need thereof comprising administering to said patient an effective ACE inhibitory amount of perindopril (preferably perindopril t-butylamine monohydrate) as provided according to the present invention.

The present invention also provides use of perindopril as provided according to the present invention (preferably perindopril t-butylamine monohydrate) in the manufacture of a medicament for inhibiting ACE.

A patient can be in need of treatment to inhibit ACE, for example when the patient is suffering from hypertension, chronic congestive heart failure, or the like. Inhibition of ACE reduces levels of angiotensin II and thus inhibits the vasopressor, hypertensive and hyperaldosteronemic effects caused thereby. Inhibition of ACE would also potentiate endogenous levels of bradykinin. An effective ACE inhibitory amount of perindopril as provided according to the present invention is that amount which is effective in inhibiting ACE in a patient in need thereof which results, for example, in a hypotensive effect.

In effecting treatment of a patient, perindopril as provided according to the present invention can be administered in any form or mode which makes the compound bioavailable in effective amounts, including oral and parenteral routes. For example, perindopril as provided according to the present invention can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated and the stage of the disease.

Perindopril as provided according to the present invention can be administered in the form of pharmaceutical compositions or medicaments which are prepared by combining the perindopril according to the present invention with pharmaceutically acceptable carriers, diluents or excipients therefor, the proportion and nature of which are determined by the chosen route of administration, and standard pharmaceutical practice.

In another embodiment, the present invention provides pharmaceutical compositions comprising an effective ACE inhibitory amount of perindopril as provided according to the present invention (preferably perindopril t-butylamine monohydrate), together with one or more pharmaceutically acceptable carriers, diluents or excipients therefor.

By "pharmaceutically acceptable" it is meant that the carrier, diluent or excipient must be compatible with perindopril as provided according to the present invention, and not be deleterious to a recipient thereof.

The pharmaceutical compositions or medicaments are prepared in a manner well known in the pharmaceutical art. The carrier, diluent or excipient may be a solid, semi-solid, or liquid material, which can serve as a vehicle or medium for the active ingredient. Suitable carriers, diluents or excipients are well known in the art. Pharmaceutical compositions according to the present invention may be adapted for oral or parenteral use and may be administered to the patient in the form of tablets, capsules, suppositories, solutions, suspensions or the like.

The pharmaceutical compositions may be administered orally, for example, with an inert diluent or with an edible carrier. They may be enclosed in gelatin capsules or compressed into tablets. For the purpose of oral therapeutic administration, a monohydrate according to the present invention may be incorporated with excipients and used in the form of tablets, capsules, elixirs, suspensions, syrups and the like.

The tablets, pills, capsules, and the like may also contain one or more of the following adjuvants: binders, such as microcrystalline cellulose, gum tragacanth or gelatin; excipients, such as starch or lactose; disintegrating agents such as alginic acid, corn starch and the like; lubricants, such as magnesium stearate; glidants, such as colloidal silicon dioxide; and sweetening agents, such as sucrose or saccharin. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives. Materials used in preparing these various compositions should be pharmaceutically pure and non-toxic in the amounts used.

For the purpose of parenteral administration perindopril as provided according to the present invention may be incorporated into a solution or suspension. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; and buffers such as acetates, citrates or phosphates. The parenteral preparation can be enclosed in ampoules, disposable syringes or multiple dose vials made of glass or plastic.

The present invention will now be further illustrated by the following FIGURE and Examples, which do not limit the scope of the invention in any way.

FIG. 1: X-ray diffraction pattern of perindopril erbumine monohydrate according to the present invention. The sample was analysed using a Shimadzu-6000 x-ray diffractometer. The source used was $K_\alpha$ monochromatic radiation of Cu having wavelength of 1.5406 A°. The Divergent Slit used was 1°. The Receiving Slit was 0.30 mm. The Scintillation counter was used as the detector, with the range being from 3° to 40° (2θ) with a scan speed of 2° per minute.

EXAMPLE 1

The benzyl ester of (2S,3aS,7aS)-1-{2-[1-(ethoxycarbonyl)-(S)-butylamino]-(S)-propionyl}-octahydroindole-2-carboxylic acid, namely benzyl perindopril, (10 gms) was dissolved in isopropanol (100 ml). To the clear solution, t-butylamine (2.5 gms) and 10% w/w palladium on charcoal (2 gms) was added. The reaction mixture was hydrogenated at a pressure of 1 kg/cm² for 2 hours.

The reaction mass was filtered to remove the catalyst. The solvent was concentrated under vacuum and isopropanol was replaced by simultaneous addition of ethyl acetate. The solids obtained were cooled to 0 EC and filtered to obtain perindopril erbumine (7.8 gms).

EXAMPLE 2

Perindopril erbumine (10 gms) was suspended in acetone (80 ml). To this was added water (0.4 ml) and the contents heated to dissolve the solids and cooled to ambient. The resulting slurry was filtered to obtain perindopril erbumine monohydrate (9.4 gms).

EXAMPLE 3

Perindopril erbumine (20 gms) was suspended in ethyl acetate (300 ml). To this was added water (1.5 ml) and the contents heated to dissolve the solids and cooled to 10 EC. The resulting slurry was filtered to obtain perindopril erburnine monohydrate (17 gms).

EXAMPLE 4

Perindopril erbumine (5 gms) was suspended in acetonitrile (75 ml). To this was added water (0.4 ml) and the contents heated to dissolve the solids and cooled to 0 EC. The resulting slurry was filtered to obtain perindopril erbumine monohydrate (2.9 gms).

EXAMPLE 5

Perindopril erbumine (20 gms) was suspended in ethyl acetate (300 ml). The contents were heated to dissolve the solids and cooled to 10 EC. The resulting slurry was filtered and dried in air having a relative humidity of at least 75% to give perindopril erbumine monohydrate (17 gms).

EXAMPLE 6

Preparation of perindopril erbumine monohydrate

Raw Materials:-

1. Perindopril erbumine anhydrous = 10 gm.
2. Isopropyl alcohol = 70 ml.
3. Water = 2 ml.
4. Ethyl acetate = 85 ml.

Procedure:—
1. Charge 10 gm of perindopril erbumine (anhydrous) in round bottom flask. Add 70 ml isopropyl alcohol. Stir for ½ hr. (around 95% product dissolved).
2. Add 2 ml of water. Stir for 15 min (clear solution obtained).
3. Stir reaction mass at 38-40° C. for 2 hrs.
4. Distill out isopropyl alcohol completely under vacuum (below 600 mm) below 40° C. (Gel type material observed.)
5. Charge 30 ml ethyl acetate. Stir for 15 min below 40° C. (clear solution observed). Distill under vacuum below 40° C. (semi-solid observed).
6. Charge 40 ml ethyl acetate at 36-38° C. Stir for 15 min (free solid observed).
7. Stir 1 hr at room temperature (25-30° C.). (Free crystalline solid observed.)
8. Cool to 10° C. Stir for 2 hrs.
9. Filter solid and wash with 15 ml ethyl acetate. Suck dry for 2 hrs.
10. Dry under vacuum below 40° C. for 12 hrs.

Water Content=3.2-3.8%

M.P=145-150° C.

EXAMPLE 7

The following tablets were prepared:

(a) Formulation I:

| | Strengths | | |
|---|---|---|---|
| Ingredients | 2 mg | 4 mg | 8 mg |
| Perindopril Erbumine Monohydrate | 2 mg | 4 mg | 8 mg |
| Maize starch | 5 mg | 10 mg | 20 mg |
| Lactose anhydrous | 12.5 mg | 25.0 mg | 100.0 mg |
| Microcrystalline cellulose | 25.10 mg | 50.20 mg | 100.40 mg |
| Magnesium stearate | 0.4 | 0.8 | 1.6 |
| Total weight | 45.0 mg | 90.0 mg | 180.0 mg |

Procedure: Sift the above ingredients through respective sieves. Mix the ingredients in a suitable blender. Compress the tablets in the suitable toolings.

(b) Formulation II:

| | Strengths | | |
|---|---|---|---|
| Ingredients | 2 mg | 4 mg | 8 mg |
| Perindopril Erbumine Monohydrate | 2 mg | 4 mg | 8 mg |
| Maize starch | 10 mg | 10 mg | 10 mg |
| Lactose anhydrous | 25 mg | 25.0 mg | 25.0 mg |
| Microcrystalline cellulose | 52.2 mg | 49.20 mg | 45.20 mg |
| Yellow oxide of Iron | — | 1.0 | — |
| Red oxide of Iron | — | — | 1.0 |
| Hydrogenated castor oil | 0.8 mg | 0.8 mg | 0.8 mg |
| Total weight | 90.0 mg | 90.0 mg | 90.0 mg |

Procedure:
1) Dissolve Perindopril Erbumine Monohydrate in ethanol.
2) Granulate the above ingredients except hydrogenated castor oil with the above solution. Dry the granules and size.
3) Lubricate with hydrogenated castor oil in suitable blender. Compress the granules in the suitable tooling

The invention claimed is:

1. A process for preparing a pharmaceutically acceptable salt of perindopril of formula (I) from a protected precursor compound of formula (II)

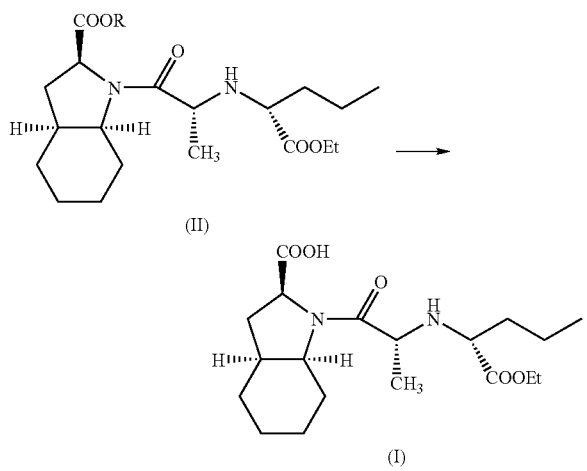

wherein R represents a carboxyl protecting group, which process comprises subjecting a compound of formula (II) to deprotection of the carboxylic group COOR attached to the heterocyclic ring so as to yield the corresponding free acid, which deprotection is carried out in the presence of a base which forms a pharmaceutically acceptable salt with said free acid formed by said deprotection.

2. A process according to claim 1, wherein R represents optionally substituted aralkyl.

3. A process according to claim 2, wherein R represents unsubstituted benzyl.

4. A process according to claim 2, wherein R represents 4-halo substituted, or 4-$C_{1-4}$ alkoxy substituted benzyl.

5. A process according to claim 4, wherein R represents 4-Cl benzyl, or 4-methoxy benzyl.

6. A process according to claim 1, wherein said deprotection comprises hydrogenolysis in the presence of a noble metal catalyst.

7. A process according to claim 6, wherein the noble metal catalyst comprises palladium-on-charcoal.

8. A process according to claim 1, wherein said base comprises t-butylamine.

9. A process for preparing perindopril t-butylamine from a protected precursor compound of formula (II)

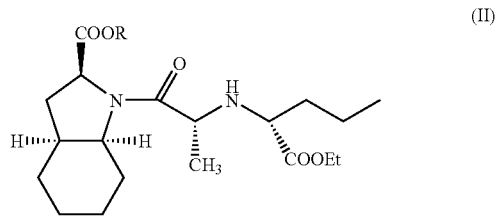

wherein R represents a carboxyl protecting group, which process comprises subjecting a compound of formula (II) to deprotection of the carboxylic group COOR attached to the heterocyclic ring so as to yield the corresponding free acid, which deprotection is carried out in the presence of t-butylamine so as to form the t-butylamine salt of perindopril.

10. A process according to claim 9, wherein R represents unsubstituted benzyl.

11. A process according to claim 9, wherein deprotection comprises hydrogenolysis in the presence of palladium-on-charcoal.

12. A process according to claim 1, which further comprises hydrating a pharmaceutically acceptable salt of perindopril obtained by said process so as to yield a pharmaceutically acceptable salt of hydrated perindopril of formula (Ia)

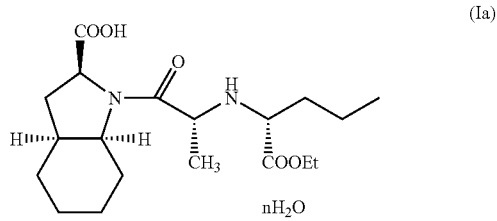

wherein n is an integer of 1 to 5, or a reciprocal of integers 2 to 5.

13. A process according to claim 12, wherein n is 1.

14. A process for preparing a monohydrate of a pharmaceutically acceptable salt of perindopril, which process comprises hydrating a pharmaceutically acceptable salt of perindopril so as to yield said monohydrate.

15. A process according to claim 12, wherein perindopril t-butylamine is hydrated to yield perindopril-t-butylamine monohydrate.

* * * * *